United States Patent [19]

Furukawa

[11] Patent Number: 4,501,281
[45] Date of Patent: Feb. 26, 1985

[54] ELECTRONIC SPHYGMOMANOMETER

[75] Inventor: Toshio Furukawa, Yamatokoriyama, Japan

[73] Assignee: Sharp Kabushiki Kaisha, Osaka, Japan

[21] Appl. No.: 450,042

[22] Filed: Dec. 15, 1982

[30] Foreign Application Priority Data

Dec. 18, 1981 [JP] Japan .............................. 56-205739

[51] Int. Cl.³ .............................................. A61B 5/02
[52] U.S. Cl. ..................................... 128/680; 128/677
[58] Field of Search ................ 128/672, 677, 680–683

[56] References Cited

U.S. PATENT DOCUMENTS

| 4,137,907 | 2/1979 | Jansen et al. | 128/681 |
| 4,188,955 | 2/1980 | Sakamoto et al. | 128/680 |
| 4,273,136 | 6/1981 | Kubo et al. | 128/680 |
| 4,356,827 | 11/1982 | Uemura et al. | 128/680 |
| 4,408,614 | 10/1983 | Weaver et al. | 128/680 |

FOREIGN PATENT DOCUMENTS 2087238  5/1982  United Kingdom ............... 128/680

Primary Examiner—Lee S. Cohen
Assistant Examiner—Angela D. Sykes
Attorney, Agent, or Firm—Birch, Stewart, Kolasch & Birch

[57] ABSTRACT

An electronic sphygmomanometer includes a digital recognition system for detecting the Korotkoff sounds. A digital signal representing the level of an output signal of a pickup sensor is introduced into the recognition system. The recognition system detects peaks included in the digital signal applied thereto. A first determination is carried out as to whether two adjacent peaks have a level difference greater than a preselected difference. A second determination is also carried out as to whether the two peaks appear within a predetermined period of time. If affirmative answers are obtained at the two determinations, the recognition system develops a detection output which indicates that the introduced signal relates to the Korotkoff sounds.

4 Claims, 45 Drawing Figures

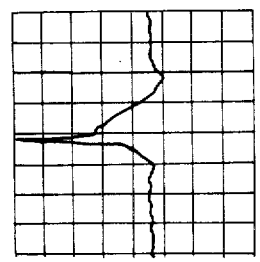
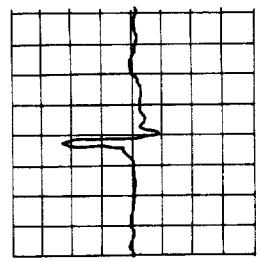
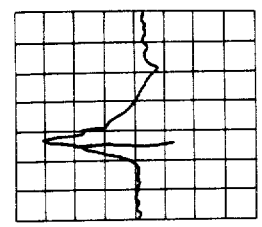
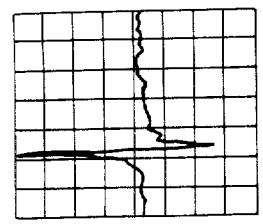
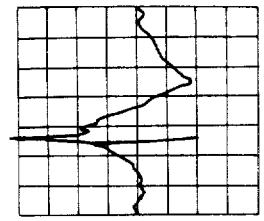
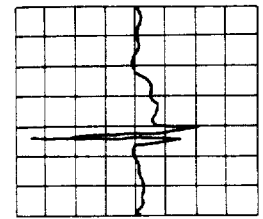
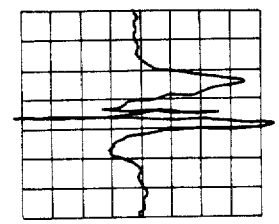
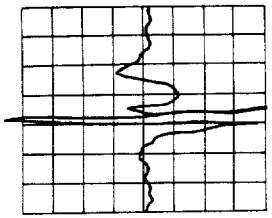
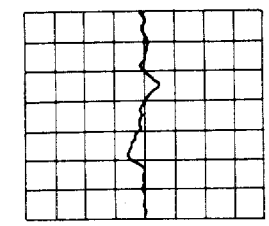
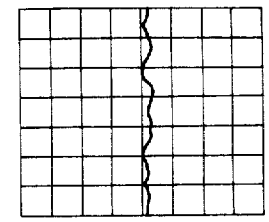

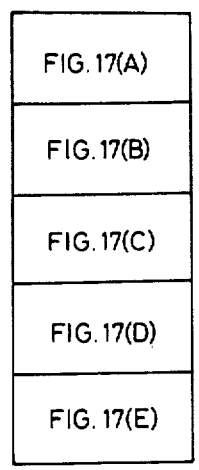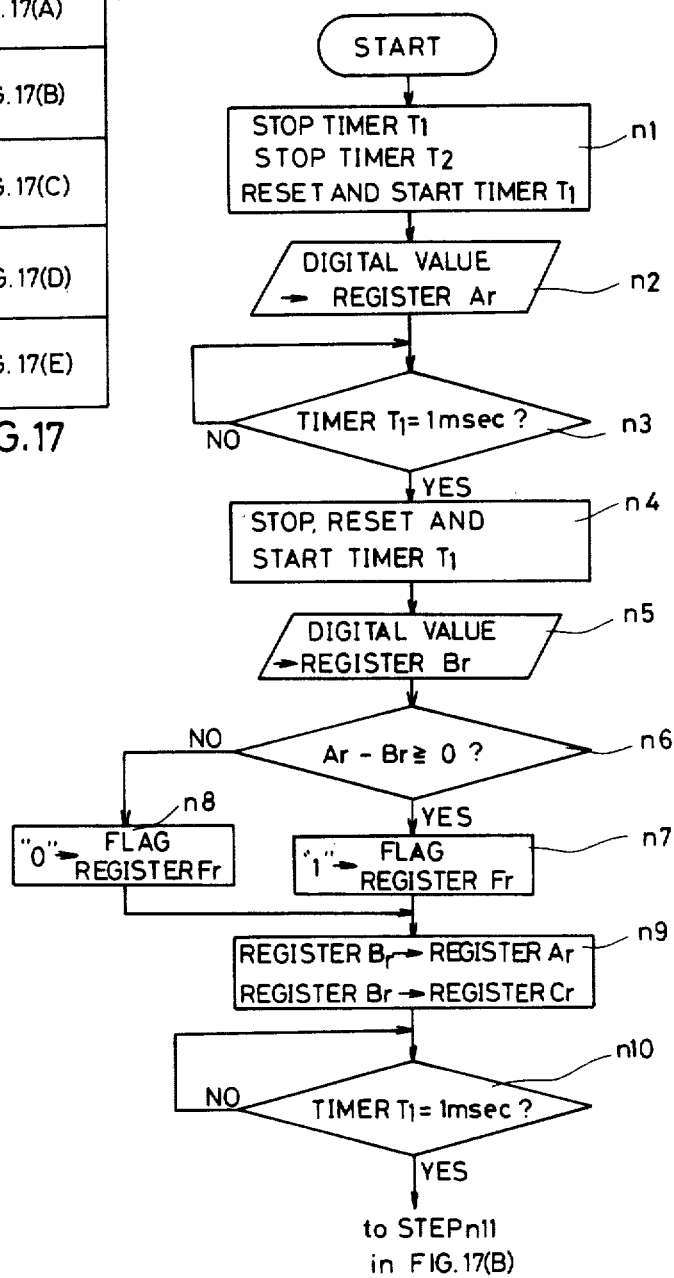
FIG. 17(A)

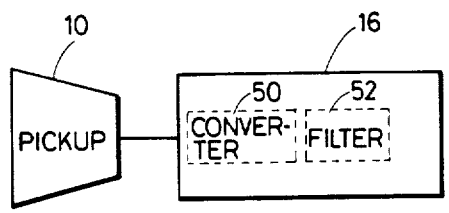
F I G. 22
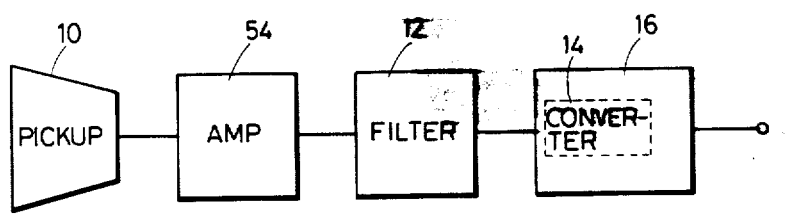
F I G. 23
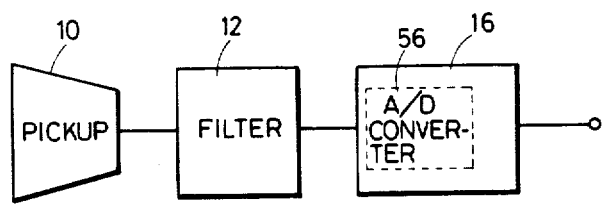
F I G. 24

ELECTRONIC SPHYGMOMANOMETER

BACKGROUND AND SUMMARY OF THE INVENTION

The present invention relates to an electronic sphygmomanometer or to an automatic indirect blood pressure measuring device.

An automatic indirect blood pressure measuring device has been developed, which utilizes the Korotkoff sounds, or blood vessel sounds derived from a microphone positioned under an arm cuff. In such a device, first a high pressure is applied to the arm cuff through the use of an air pump and, then, the pressure applied to the arm cuff is gradually reduced at a rate, for example, 2 to 4 mmHg/sec. During the reduction procedure of the applied pressure, the Korotkoff sounds appear at the systolic pressure point, and the Korotkoff sounds disappear at the diastolic pressure point.

A typical control system for an electronic sphygmomanometer is disclosed in U.S. Pat. No. 4,273,136, "ELECTRONIC SPHYGMOMANOMETER" issued on June 16, 1981.

In such an electronic sphygmomanometer, it is strictly required that the Korotkoff sounds are distinguished from noises in order to ensure an accurate detection of the blood pressure. In the conventional system, the microphone output signal is passed through a low-pass filter or a bandpass filter, and the filter output signal is applied to a comparator to determine the peak value of the obtained signal. However, the frequency characteristics of the Korotkoff sounds are variable depending upon the person to be measured. Especially, if a person has hardened arteries or thick subcutaneous fat, the determination as to whether the microphone output signal is the Korotkoff sounds or not is very difficult.

Accordingly, an object of the present invention is to provide a detection system for an electronic sphygmomanometer, which ensures an accurate detection of the blood pressure.

Another object of the present invention is to provide a digitally controlled detection system for an electronic sphygmomanometer, which ensures an accurate detection of the Korotkoff sounds.

Other objects and further scope of applicability of the present invention will become apparent from the detailed description given hereinafter. It should be understood, however, that the detailed description and specific examples, which indicating preferred embodiments of the invention, are given by way of illustration only, since various changes and modifications within the spirit and scope of the invention will become apparent to those skilled in the art from this detailed description.

To achieve the above objects, pursuant to an embodiment of the present invention, the microphone output is applied to an A/D converter via a filter. The thus obtained digital signal is introduced into a microcomputer to check the characteristics of the digital signal. More specifically, the digital signal is applied to a determination circuit at a predetermined interval. The determination circuit first detects the leading edge peak and the trailing edge peak of the output signal derived from the A/D converter. Then, the determination is conducted as to whether the value difference between the leading edge peak and the trailing edge peak is greater than a preselected value, and as to whether the time interval between the peaks is within a preselected period of time.

BRIEF DESCRIPTION OF THE DRAWINGS

The present invention will be better understood from the detailed description given hereinbelow and the accompanying drawings which are given by way of illustration only, and thus are not limitative of the present invention and wherein:

FIGS. 7(A), 8(A), 9(A), 10(A) and 11(A) are graphs showing output signals of a pickup sensor included in the electronic sphygmomanometer of FIG. 1 when a person having arteriosclerosis is being measured;

FIGS. 7(B), 8(B), 9(B), 10(B) and 11(B) are graphs showing output signals of a filter included in the electronic sphygmomanometer of FIG. 1 when the pickup sensor outputs of FIGS. 7(A), 8(A), 9(A), 10(A) and 11(A) are applied to the filter, respectively;

FIGS. 17, 17(A), 17(B), 17(C), 17(D) and 17(E) are flow charts for explaining an operational mode of the electronic sphygmomanometer of FIG. 1;

FIG. 22 is a schematic block diagram of still another embodiment of an electronic sphygmomanometer according to the present invention;

FIG. 23 is a schematic block diagram of yet another embodiment of an electronic sphygmomanometer according to the present invention; and FIG. 24 is a schematic block diagram of a further embodiment of an electronic sphygmomanometer according to the present invention.

DESCRIPTION OF THE PREFERRED EMBODIMENTS

Figure 1:
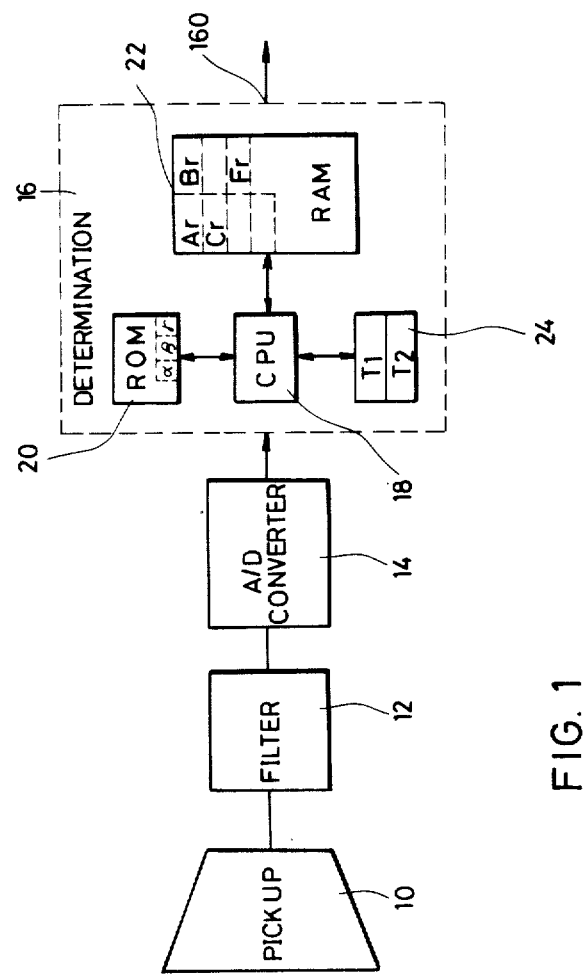
FIG. 1 is a schematic block diagram of an embodiment of an electronic sphygmomanometer according to the present invention.

FIG. 1 schematically shows an embodiment of an electronic sphygmomanometer of the present invention, which includes a pickup sensor 10 for detecting the sound or vibration derived from the artery. An output signal of the pickup sensor 10 is applied to a filter 12 which is preferably a lowpass filter below 40 Hz or a bandpass filter of 10 Hz to 40 Hz. An output signal of the filter 12 is introduced into an analog-to-digital converter 14 which develops a digital signal of eight (8) bit construction in response to the level of the signal applied thereto. The thus developed digital signal is introduced into a determination system 16 which performs the determination as to whether the introduced signal is derived from the Korotkoff sounds. If an affirmative answer is obtained, the determination system 16 develops a determination output at an output terminal 160.

The determination system 16 includes a central processor unit 18, a read only memory 20 and a random access memory 22 incorporated in a single chip microcomputer. The read only memory 20 stores program orders for conducting the programmed operation, and constants $\alpha$, $\beta$ and $\gamma$ for controlling the operation of the electronic sphygmomanometer of the present invention. The random access memory 22 includes register sections Ar, Br and Cr, and a flag section Fr. The determination system 16 further includes a timer 24 ($T_1$ and $T_2$).

The determination system 16 introduces the digital signal developed from the analog-to-digital converter 14 in a predetermined interval. The determination system 16 functions to detect peaks of the digital signal in the level increasing process and in the level decreasing process. The determination system 16 performs the determination as to whether the level difference between the peaks is greater than a predetermined value and as to whether a time interval between the peaks is within a preselected period of time, thereby recognizing the Korotkoff sounds.

Figure 2A:
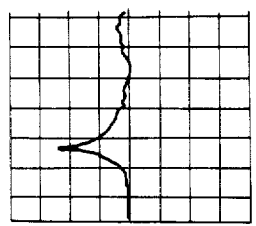
FIGS. 2(A), 3(A), 4(A), 5(A) and 6(A) are graphs showing output signals of a pickup sensor included in the electronic sphygmomanometer of FIG. 1 when a generally healthy person is being measured.
Figure 3A:
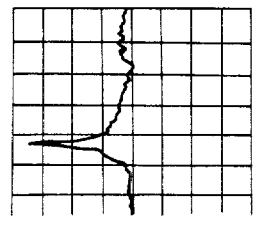
Figure 4A:
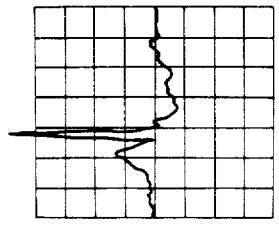
Figure 5A:
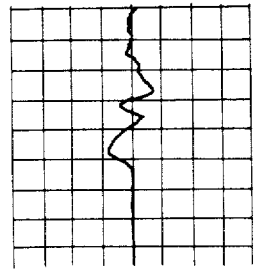
Figure 6A:
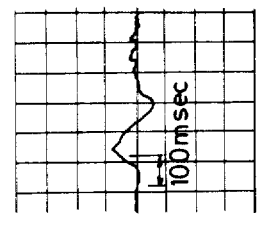
Figure 16A:
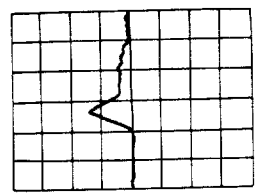
FIGS. 12(A), 13(A), 14(A), 15(A) and 16(A) are graphs showing output signals of a pickup sensor included in the electronic sphygmomanometer of FIG. 1 when a person having thick subcutaneous fat is being measured.
Figure 15A:
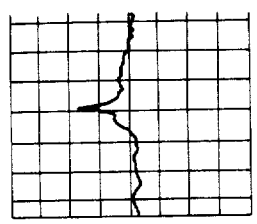
Figure 15B:
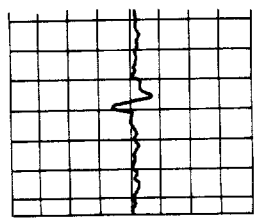
Figure 14A:
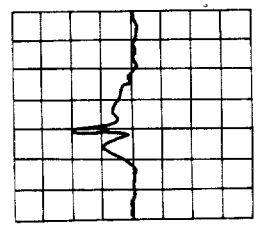
Figure 14B:
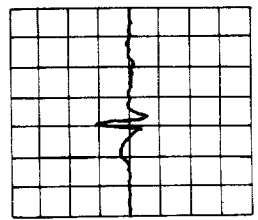
Figure 13A:
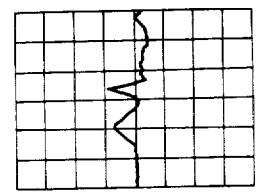
Figure 13B:
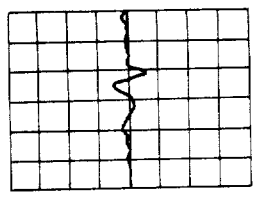
Figure 12A:
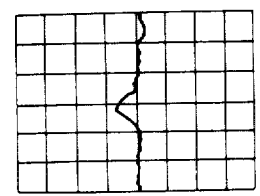

FIGS. 2(A), 3(A), 4(A), 5(A) and 6(A) show the output signals of the pickup sensor 10 of a healthy person when the pressure applied to the arm cuff varies. FIGS. 7(A), 8(A), 9(A), 10(A) and 11(A) show the pickup sensor output signals when a person having hardened arteries is being measured. FIGS. 12(A), 13(A), 14(A), 15(A) and 16(A) show the pickup sensor output signals when a person having thick subcutaneous fat is being measured. Furthermore, FIGS. 2(A), 7(A) and 12(A) show the pickup sensor output signals when the cuff pressure is above the systolic pressure. FIGS. 3(A), 8(A) and 13(A) show the pickup sensor output signals when the cuff pressure is at the systolic pressure point. FIGS. 4(A), 9(A) and 14(A) show the pickup sensor output signals when the cuff pressure is between the systolic pressure and the diastolic pressure. FIGS. 5(A), 10(A) and 15(A) show the pickup sensor output signals when the cuff pressure is at the diastolic pressure point. FIGS. 6(A), 11(A) and 16(A) show the pickup sensor output signals when the cuff pressure is lower than the diastolic pressure.

Figure 2B:
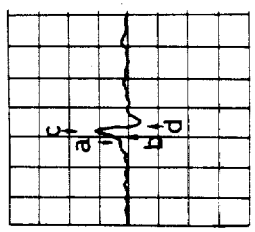
FIGS. 2(B), 3(B), 4(B), 5(B) and 6(B) are graphs showing output signals of a filter included in the electronic sphygmomanometer of FIG. 1 when the pickup sensor outputs of FIGS. 2(A), 3(A), 4(A), 5(A) and 6(A) are applied to the filter, respectively.
Figure 3B:
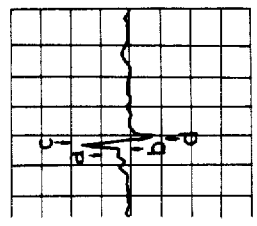
Figure 16B:
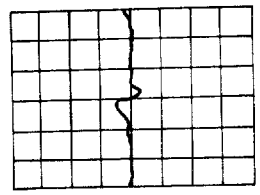
FIGS. 12(B), 13(B), 14(B), 15(B) and 16(B) are graphs showing output signals of a filter included in the electronic sphygmomanometer of FIG. 1 when the pickup sensor outputs of FIGS. 12(A), 13(A), 14(A), 15(A) and 16(A) are applied to the filter, respectively.

The thus obtained pickup sensor output signal is applied to the filter 12. In a preferred form, the filter 12 is a combined construction of a highpass filter having the cut-off frequency of 20 Hz and having the cut-off characteristic of 6 dB/oct., and a lowpass filter having the cut-off frequency of 40 Hz and the cut-off characteristic of 12 dB/oct. FIG. 2(B) shows an output signal of the filter 12 when the pickup sensor output signal of FIG. 2(A) is applied to the filter 12. FIG. 3(B) shows an output signal of the filter 12 when the signal of FIG. 3(A) is applied to the filter 12. In a same manner, FIG. 16(B) shows an output signal of the filter 12 when the signal of FIG. 16(A) is applied to the filter 12.

As already discussed above, the filter output signal is applied to the determination system 16 via the analog-to-digital converter 14. The determination system 16 determines that the input signal includes the Korotkoff sound components when the signal of FIG. 3(B), 4(B), 5(B), 8(B), 9(B), 10(B), 13(B), 14(B) or 15(B) is developed from the filter 12, and then the determination system 16 develops the determination output through the output terminal 160.

The register Ar included in the determination system 16 stores the digital value of the last sampled signal level developed from the filter 12. The register Br stores the digital value of the newly sampled signal level developed from the filter 12. The register Cr stores the digital value of the peak level of the sampled signal. Furthermore, the flag register Fr memorizes the inclination or slope of the signal developed from the filter 12. When the filter output signal is in the increasing process, a data "0" is memorized in the flag register Fr. When the filter output signal is in the decreasing process, a data "1" is memorized in the flag register Fr. The timer $T_1$ measures 1 msec. which will be used to determine the sampling time. The timer $T_2$ functions to measure the time interval between two peaks which will appear in the output signal derived from the filter 12.

An operational mode of the determination system 16 will be described with reference to FIGS. 17, 17(A), 17(B), 17(C), 17(D) and 17(E). The following operation is controlled by the micro-orders stored in the read only memory 20.

FIG. 17(A) shows an operation for setting an initial value before conducting the recognition operation of the Korotkoff sounds.

At the step n1, the counting operation of the timer $T_2$ is stopped, and the timer $T_1$ is reset to start a new counting operation. The digital value developed from the analog-to-digital converter 14 is introduced into the register Ar at the step n2. The sampling operation is conducted in accordance with the counting operation of the timer $T_1$. That is, the sampling operation is conducted with the time interval of 1 msec. More specifically, when 1 msec. passed, the program is advanced from the step n3 to the step n4 to re-start the counting operation of the timer $T_1$. Then, the digital value developed from the analog-to-digital converter 14 is introduced into the register Br at the step n5. At the following step n6 a determination is conducted as to whether the digital value stored in the register Ar is greater than or equal to the digital value stored in the register Br. If an affirmative answer is obtained at the step n6, the program is advanced to the step n7 to set "1" in the flag register Fr. If an affirmative answer is not obtained, the program is advanced to the step n8 to set "0" in the flag register Fr. That is, when the level of the output signal of the filter 12 is in the increasing process, the data "0" is memorized in the flag register Fr. When the output signal of the filter 12 is in the decreasing process, the data "1" is memorized in the flag register Fr. At the following step n9, the digital value stored in the register Br is transferred to the register Ar as the last sampled data. Furthermore, the digital value stored in the register Br is transferred to the register Cr as the peak value. When another 1 msec. has passed, the program is advanced from the step n10 to the following steps.

Figure 17B:
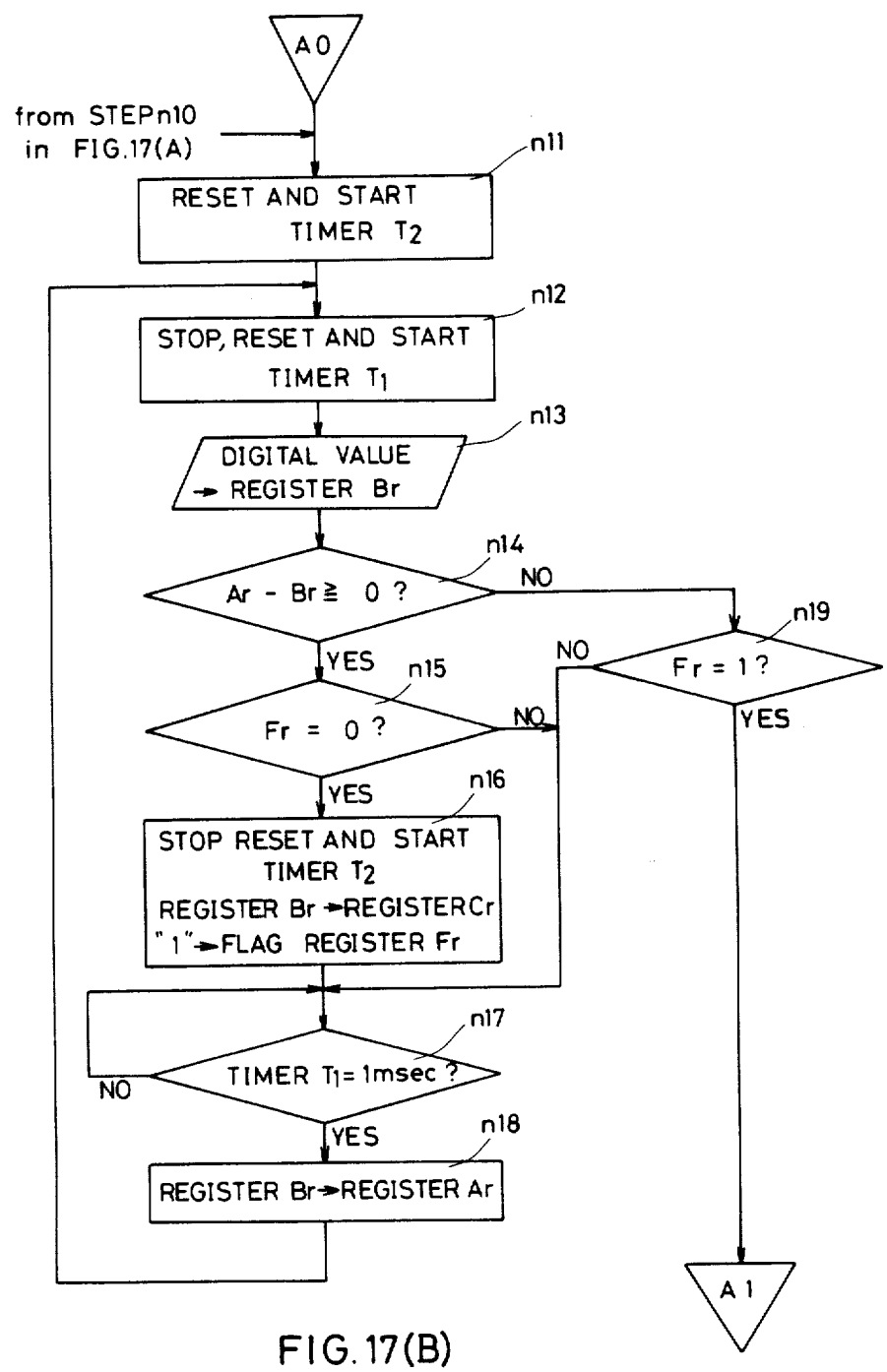
Figure 17C:
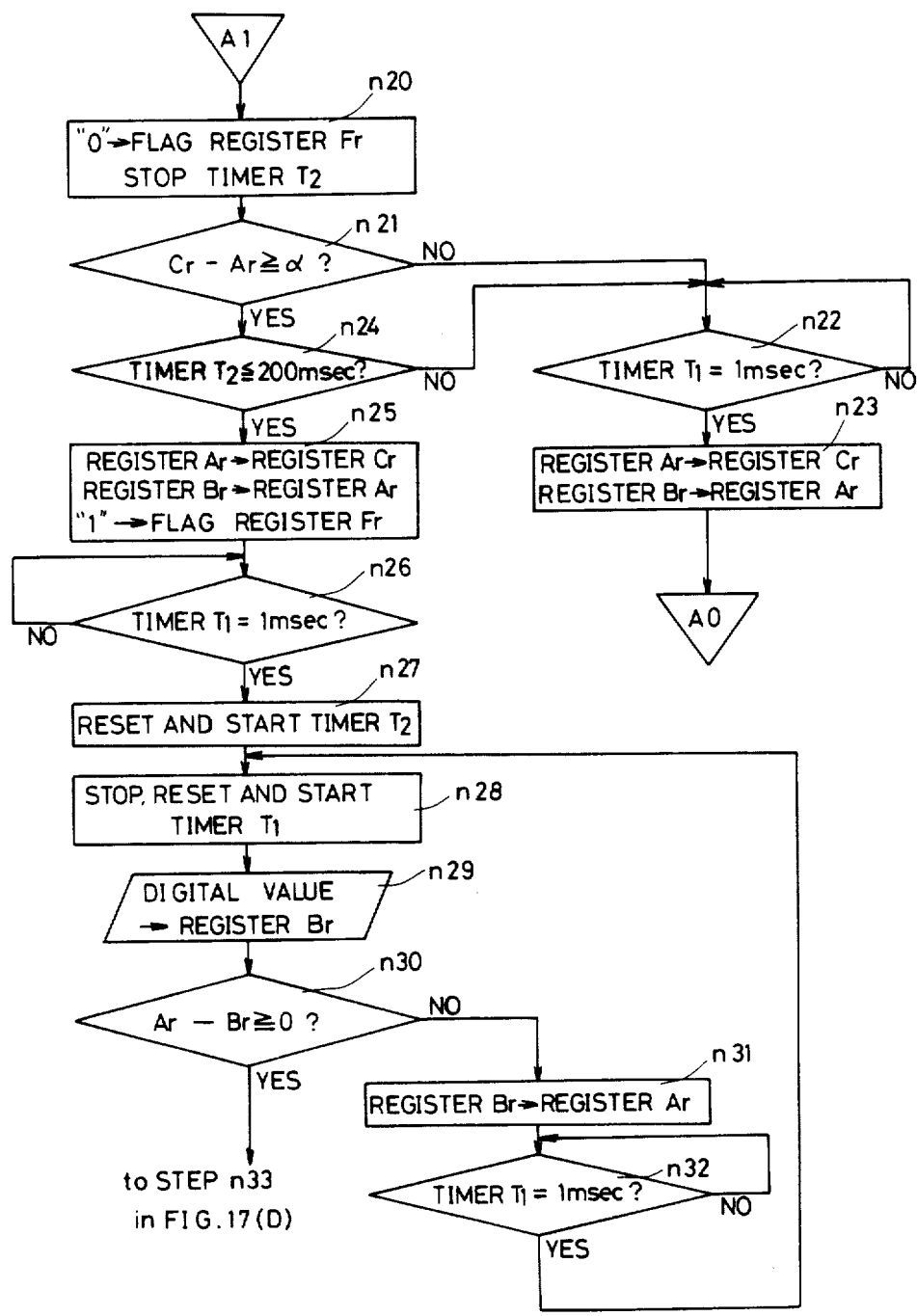

FIGS. 17(B) and 17(C) (steps n11 through n26) show an operation for detecting a first negative (trailing edge) peak in the filter output signal, and for checking whether the introduced signal relates to the Korotkoff sounds.

At the steps n11 and n12, the timers $T_1$ and $T_2$ are reset and controlled to start the new counting operations. The new digital data is introduced into the register Br at the step n13. A determination is conducted at the step n14 as to whether the digital value stored in the register Ar is greater than or equal to the digital value newly introduced into the register Br. When an affirmative answer is obtained, that is when the level of the filter output signal is in the decreasing process, the program is advanced to the step n15 to check the condition of the flag register Fr which stores the information as to whether the last sampling data showed an increasing or decreasing signal. When the last sampling data showed an increasing signal, the operation is advanced to the step n16 to transfer the digital value stored in the register Br to the register Cr as the positive (leading edge) peak value. Then, the data "1" is set in the flag register Fr, and the counting operation of the timer $T_2$ is restarted. When 1 msec. is counted by the timer $T_1$, the program is advanced from the step n17 to the step n18 to transfer the digital value stored in the register Br to the register Ar.

Then, the operation is returned to the step n12 to repeat the above-mentioned operation.

If a negative answer is obtained at the level of the step n14, that is when the newly introduced filter output signal is in the increasing process, the program is advanced from the step n14 to the step n19 at which the memory state of the flag register Fr is checked. When the data "0" is stored in the flag register Fr, that is when the last sampling data showed an increasing signal, the operation is advanced from the step n19 to the step n17. Contrarily when the data "1" is detected at the step n19, that is when the last sampling data showed a decreasing signal, the determination system 16 determines that the negative (trailing edge) peak is detected. Then, the operation is advanced to the step n20 in FIG. 17(C) in order to determine as to whether the detected negative (trailing edge) peak is derived from the Korotkoff sounds.

At the step n20 in FIG. 17(C), the flag register Fr is set to "0", and the counting operation of the timer $T_2$ is stopped. A determination is conducted at the following step n21 as to whether the difference between the digital value stored in the register Cr (which represents the last peak value) and the digital value stored in the register Ar (which represents the peak value of the newly detected negative (trailing edge) peak) is greater than or equal to a predetermined value "$\alpha$". If an affirmative answer is not obtained, the system determines that the introduced signal does not relate to the Korotkoff sounds, and the operation is advanced to the step n22. When 1 msec. has been counted by the timer $T_1$, the operation is advanced from the step n22 to the step n23 at which the digital value stored in the register Ar is transferred to the register Cr, and the digital value stored in the register Br is transferred to the register Ar. Then, the operation is returned to the step n11 in FIG. 17(B).

When an affirmative answer is obtained at the step n21, the operation is advanced to the step n24 at which the time interval between the two peaks is checked. When more than 200 msec. have been passed from the last peak to the now detected peak, the system determines that the introduced signal does not relate to the Korotkoff sounds and, then, the operation is advanced to the above-mentioned step n22. When the now detected peak appeared within 200 msec. after the appearance of the last peak, the system determines that the introduced signal may relate to the Korotkoff sounds. The operation is advanced to the following step n25 at which the digital value stored in the register Ar is transferred to the register Cr as the peak value, and the digital value stored in the register Br is transferred to the register Ar as the last sampling value. Furthermore, the data "1" is set in the flag register Fr. When 1 msec. has passed, the operation is advanced from the step n26 to the step n27.

Figure 17D:
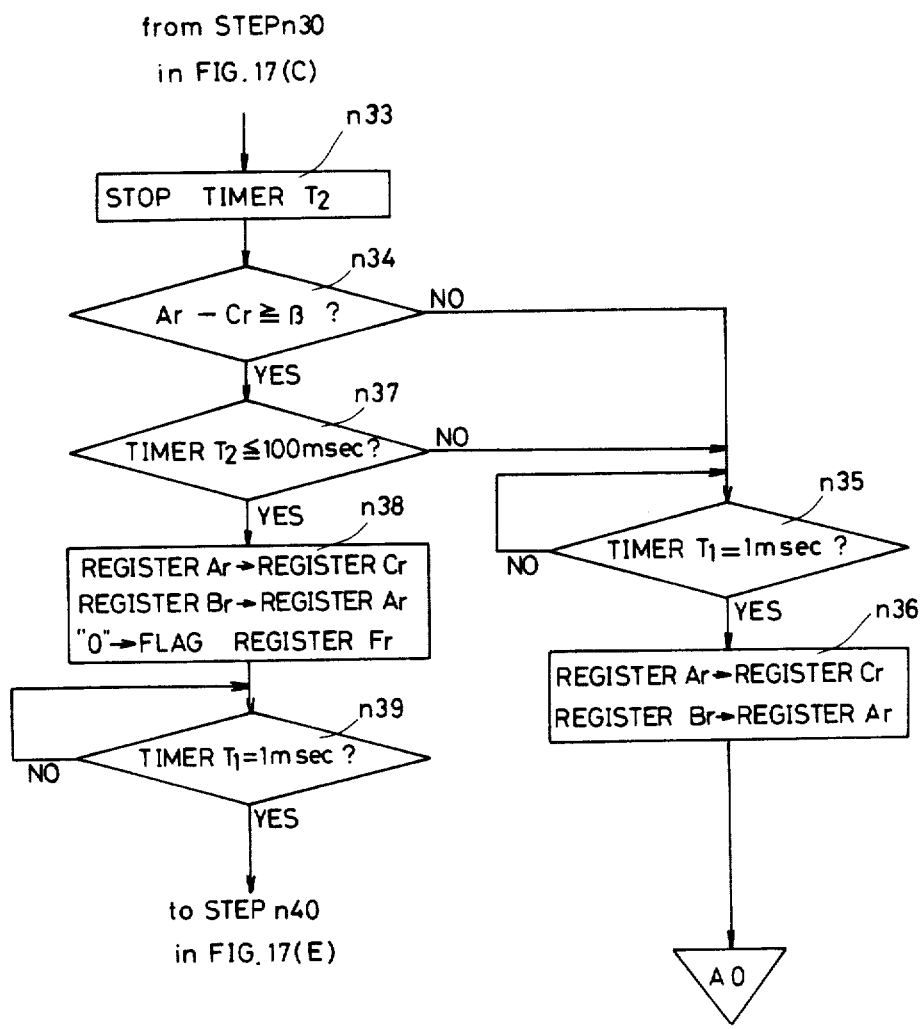

FIGS. 17(C) and 17(D) (steps n27 through n39) show an operation for detecting a positive (leading edge) peak in the filter output signal, and for checking whether the introduced signal relates to the Korotkoff sounds.

At the steps n27 and n28, the timers $T_1$ and $T_2$ are reset and controlled to start the new counting operations. The new digital data is introduced into the register Br at the step n29. A determination is conducted at the step n30 as to whether the digital value stored in the register Ar (last sampling data) is greater than or equal to the digital value introduced into the register Br. When an affirmative answer is not obtained, that is when the level of the filter output signal is increasing process, the operation is advanced to the step n31 at which the digital value stored in the register Br is transferred to the register Ar. When 1 msec. has passed, the operation is returned from the step n32 to the step n28.

When an affirmative answer is obtained at the step n30, the operation is advanced to the step n33 in FIG. 17(D). That is, when the level of the filter output signal is decreasing, the system determines that the positive (leading edge) peak is detected. Therefore, the timer $T_2$ is stopped at the step n33 and, then, the operation is advanced to the following step n34. A determination is conducted at the step n34 as to whether the difference between the now detected peak value stored in the register Ar and the last detected negative (trailing edge) peak value stored in the register Cr is greater than or equal to a predetermined value "$\beta$". If an affirmative answer is not obtained at the step n34, the system determines that the introduced signal does not relate to the Korotkoff sounds, and the operation is advanced to the step n35. When 1 msec. has passed, the program is advanced from the step n35 to the step n36 at which the digital value stored in the register Ar is transferred to the register Cr, and the digital value stored in the register Br is transferred to the register Ar. Then, the operation is returned to the step n11 in FIG. 17(B).

Contrarily when an affirmative answer is obtained at the step n34, the operation is advanced to the step n37 in order to check the time interval between the appearance of the last detected negative (trailing edge) peak and the appearance of the now detected positive (leading edge) peak. If the now detected peak appeared after 100 msec. from the appearance of the last peak, the system determines that the introduced signal does not relate to the Korotkoff sounds, and the operation is advanced to the above-mentioned step n35. When the now detected peak is within 100 msec. from the last detected peak, the system determines that the introduced signal may relate to the Korotkoff sounds, and the operation is advanced to the following step n38. The digital value stored in the register Ar is transferred to the register Cr as the peak value. The digital value stored in the register Br is transferred to the register Ar. Furthermore, a data "0" is set in the flag register Fr, and the program is advanced from the step n39 to the step n40 in FIG. 17(E) when 1 msec. has passed.

Figure 17E:
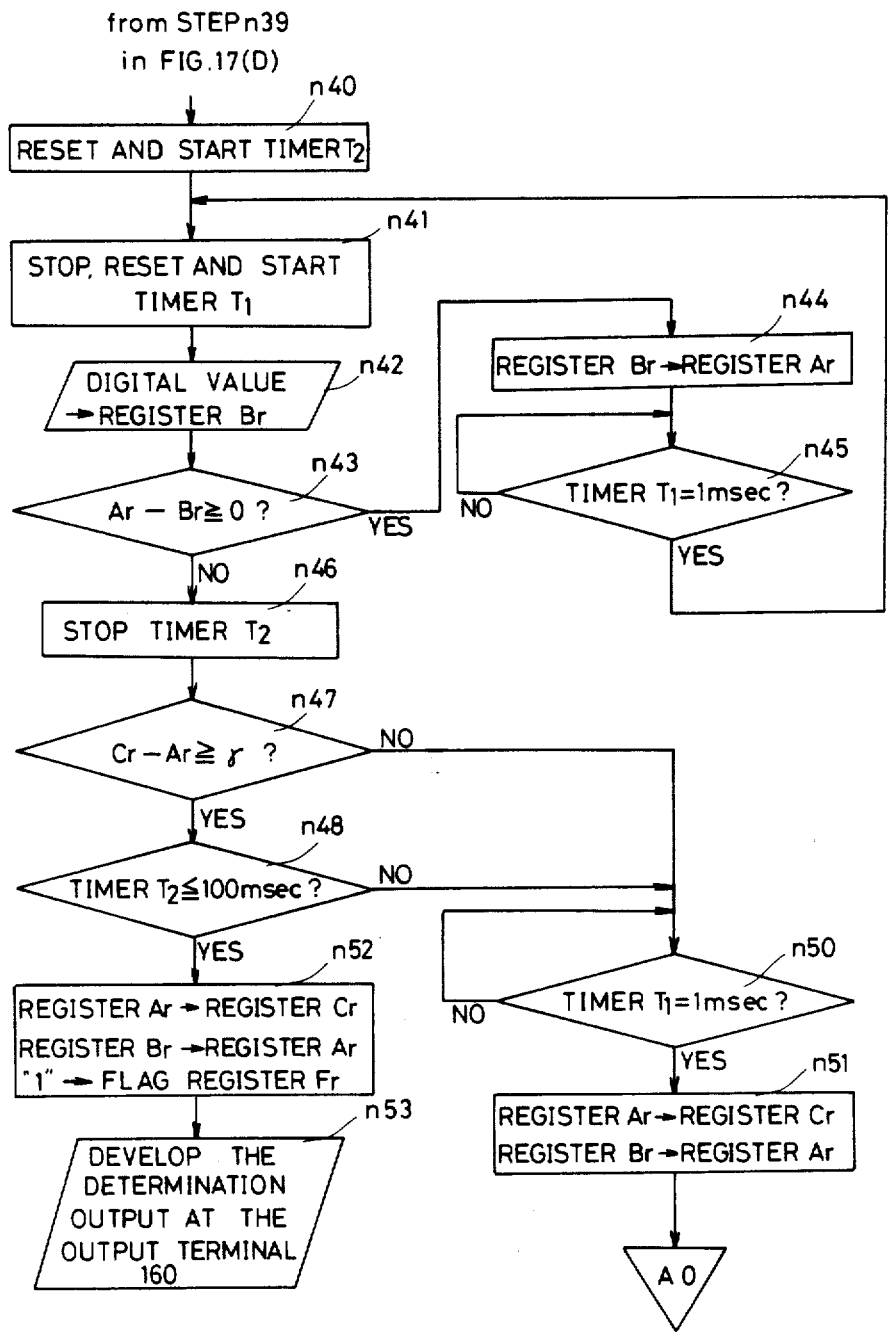

FIG. 17(E) shows an operation for detecting a sound negative (trailing edge) peak in the filter output signal, for checking whether the introduced signal relates to the Korotkoff sounds, and for developing the determination output from the output terminal 160 when the introduced signal relates to the Korotkoff sounds.

In a similar way as discussed above, the new digital value is introduced into the register Br at the step n42. A determination is carried out at the step n43 as to whether the new introduced data is in the increasing process or the decreasing process. If the level of the filter output signal is decreasing, the operation is returned from the step n43 to the step n41 through the steps n44 and n45. When the level of the filter output signal is increasing, the counting operation of the timer $T_2$ is stopped at the step n46 and the counted contents are prepared for the determination at the step n48. Another determination is conducted at the step n47 as to whether the value difference between the digital values stored in the register Cr and the register Ar is greater than or equal to a predetermined value "$\gamma$". When an affirmative answer is obtained at the step n47, still another determination is carried out at the step n48 whether the present peak is detected within 100 msec. from the detection of the lask peak. When an affirmative answer is not obtained at the step n48, the system determines that the introduced signal does not relate to the Korotkoff sounds, and the operation is returned to the step n11 in FIG. 17(B) through the steps n50 and n51. If an affirmative answer is obtained at the step n48, the system recognizes that the introduced signal relates to the Korotkoff sounds, and the operation is advanced through the step n52 to the step n53 for developing the determination output at the output terminal 160.

Figure 18:
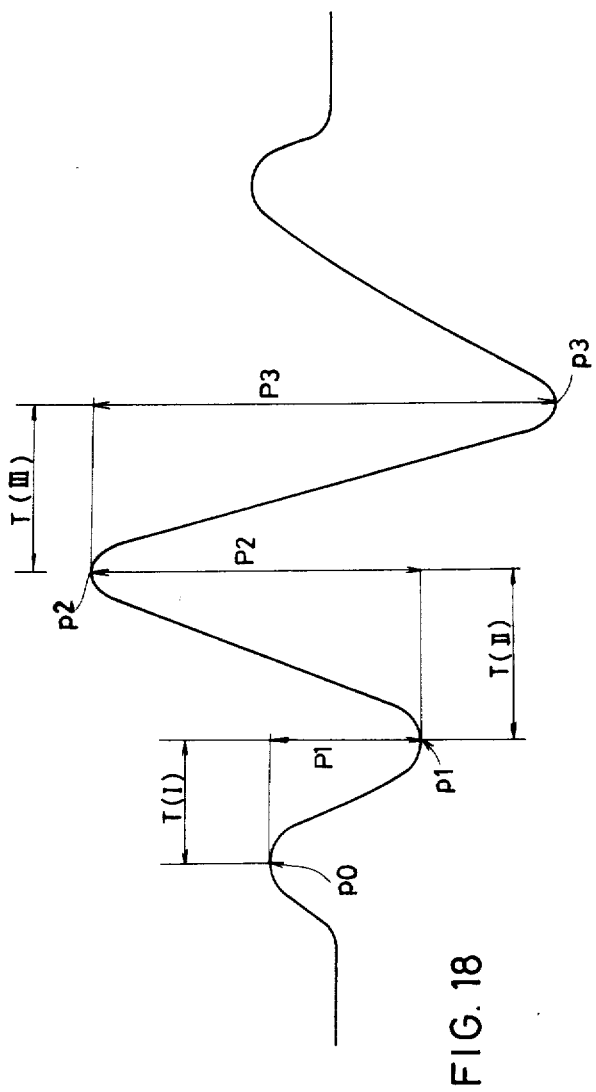
FIG. 18 is an enlarged graph of the filter output signal shown in FIG. 3(B)

The above-mentioned constants $\alpha$, $\beta$ and $\gamma$ are determined in the following manner. The constant $\alpha$ determines the minimum value of the difference $P_1$ (see FIG. 18) between the first negative (trailing edge) peak $p_1$ and the preceding positive (leading edge) peak $p_0$. The minimum value is determined taking into account the difference $P_1$ in FIG. 15(B) (filter output signal around the diastolic pressure of a person having a thick subcutaneous fat). The constant $\beta$ determines the minimum value of the difference $P_2$ between the first negative (trailing edge) peak $p_1$ and the next positive (leading edge) peak $p_2$. The minimum value is selected taking into account the difference $P_2$ in FIG. 3(B) (filter output signal at the systolic pressure of a healthy person or the difference $P_2$ in FIG. 13(B) (filter output signal at the systolic pressure of a person having a thick subcutaneous fat). Alternatively, the minimum value is selected in accordance with the difference $P_2$ in FIG. 15(B) (filter output signal around the diastolic pressure of a person having a thick subcutaneous fat). In a preferred form, the constant $\beta$ is selected at a value slightly lower than the smallest value of the abovementioned three difference $P_2$. The constant $\gamma$ determines the minimum value of the difference $P_3$ between the positive (leading edge) peak $p_2$ and the second negative (trailing edge) peak $p_3$. The constant $\gamma$ is selected at a value slightly smaller than the lower value as between the difference $p_3$ in FIG. 3(B) (filter output signal at the systolic pressure of a healthy person) and the difference $P_3$ in FIG. 13(B) (filter output signal at the systolic pressure of a person having a thick subcutaneous fat).

Figure 12B:
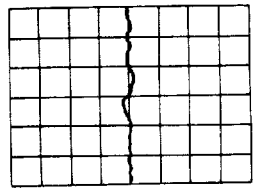

When a filter output signal as shown in FIG. 2(B), 7(B) or 12(B) is introduced into the determination system 16, the determination system 16 recognizes that the introduced signal does not relate to the Korotkoff sounds because the determination at the step n34 provides a negative answer. This is because the filter output signal has a small difference $P_2$.

Figure 19B:
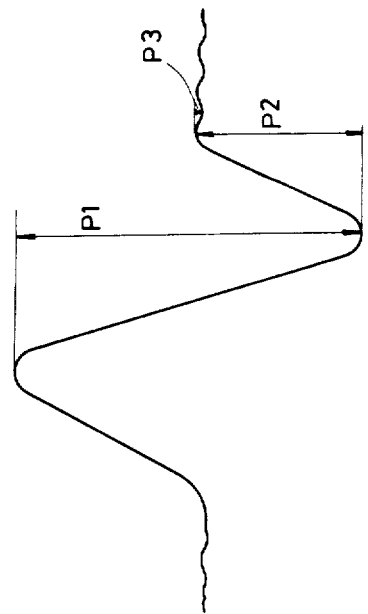
FIGS. 19(A) and 19(B) are enlarged graphs of the filter output signal shown in FIG. 16(B)
Figure 19A:
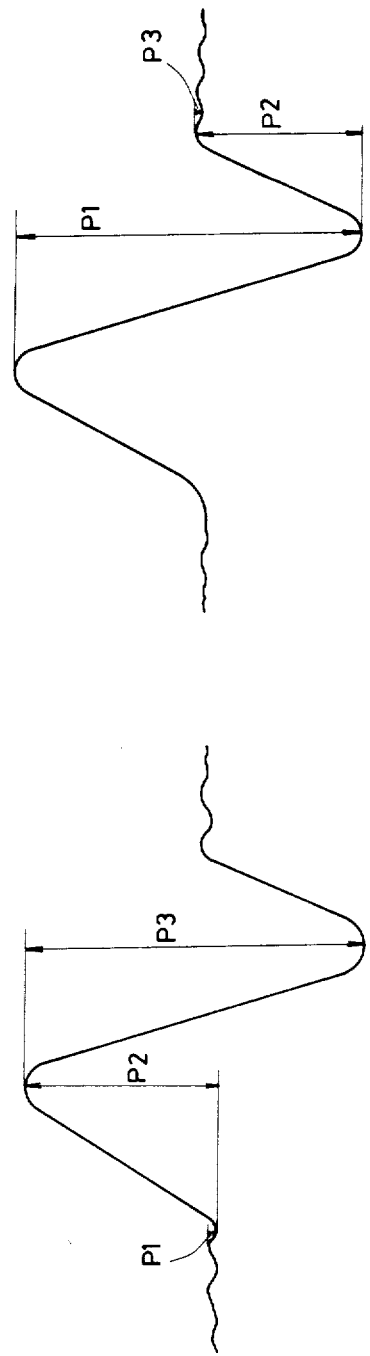

When a filter output signal as shown in FIG. 16(B) is introduced into the determination system 16, the determination system 16 determines that the introduced signal does not relate to the Korotkoff sounds because the step n34 in FIG. 17(D) or the step n47 in FIG. 17(E) provides a negative answer. This is because the introduced signal does not have the difference corresponding to the above-mentioned difference $P_1$. Accordingly, as shown in FIGS. 19(A) and 19(B), the differences $P_1$, $P_2$ and $P_3$ shown in FIG. 19(A) are considered as the differences $P_1$, $P_2$ and $P_3$ shown in FIG. 19(B), respectively.

Figure 6B:
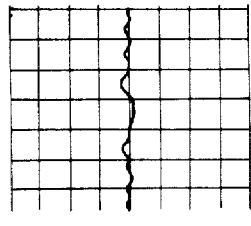

When a filter output signal as shown in FIG. 6(B) or 11(B) is introduced into the determination circuit 16, the determination circuit 16 determines that the introduced signal does not relate to the Korotkoff sounds at the determination of the step n21 shown in FIG. 17(C). This is because, it will be clear from FIGS. 6(B) and 11(B), the difference $P_1$ is very small.

The following is an operation when the filter output signal shown in FIG. 3(B) is introduced into the determination circuit through the analog-to-digital converter 14.

The difference $P_1$ in FIG. 3(B) is greater than the constant $\alpha$. In the charts of FIGS. 2(A) through 16(A) and 2(B) through 16(B), one abscissa scale represents 100 msec. In the signal of FIG. 3(B), the time difference T(I) provided between the positive (leading edge) peak $p_0$ and the first negative (trailing edge) peak $p_1$ is less than 200 msec. Accordingly, the step n21 and step n24 in FIG. 17(C) provide affirmative answers. That is, the determination operation is advanced to the step n27 through steps n25 and n26. Furthermore, the signal shown in FIG. 3(B) has the difference $P_2$ greater than the constant $\beta$. Moreover, the time interval T(II) between the first negative (trailing edge) peak $p_1$ and the positive (leading edge) peak $p_2$ is shorter than 100 msec. Accordingly, the steps n34 and n37 provide affirmative answers to advance the determination to the step n40 through the steps n38 and n39 of FIG. 17(D). The filter output signal shown in FIG. 3(B) has the difference $P_3$ greater than the constant $\gamma$. Furthermore, the time interval T(III) between the positive (leading edge) peak $p_2$ and the second negative (trailing edge) peak $p_3$ is shorter than 100 msec. Accordingly, the determination system 16 obtains the affirmative answers at the steps n47 and n48 shown in FIG. 17(E). Thus, the determination system 16 recognizes that the filter output signal relates to the Korotkoff sounds, and develops the determination output at the output terminal 160.

In a same manner, when the filter output signals shown in FIGS. 4(B), 5(B), 8(B), 9(B), 10(B), 13(B) 14(B) and 15(B) are applied to the determination system 16 via the analog-to-digital converter 14, the determination system 16 develops the determination output at the output terminal 160.

Figure 20:
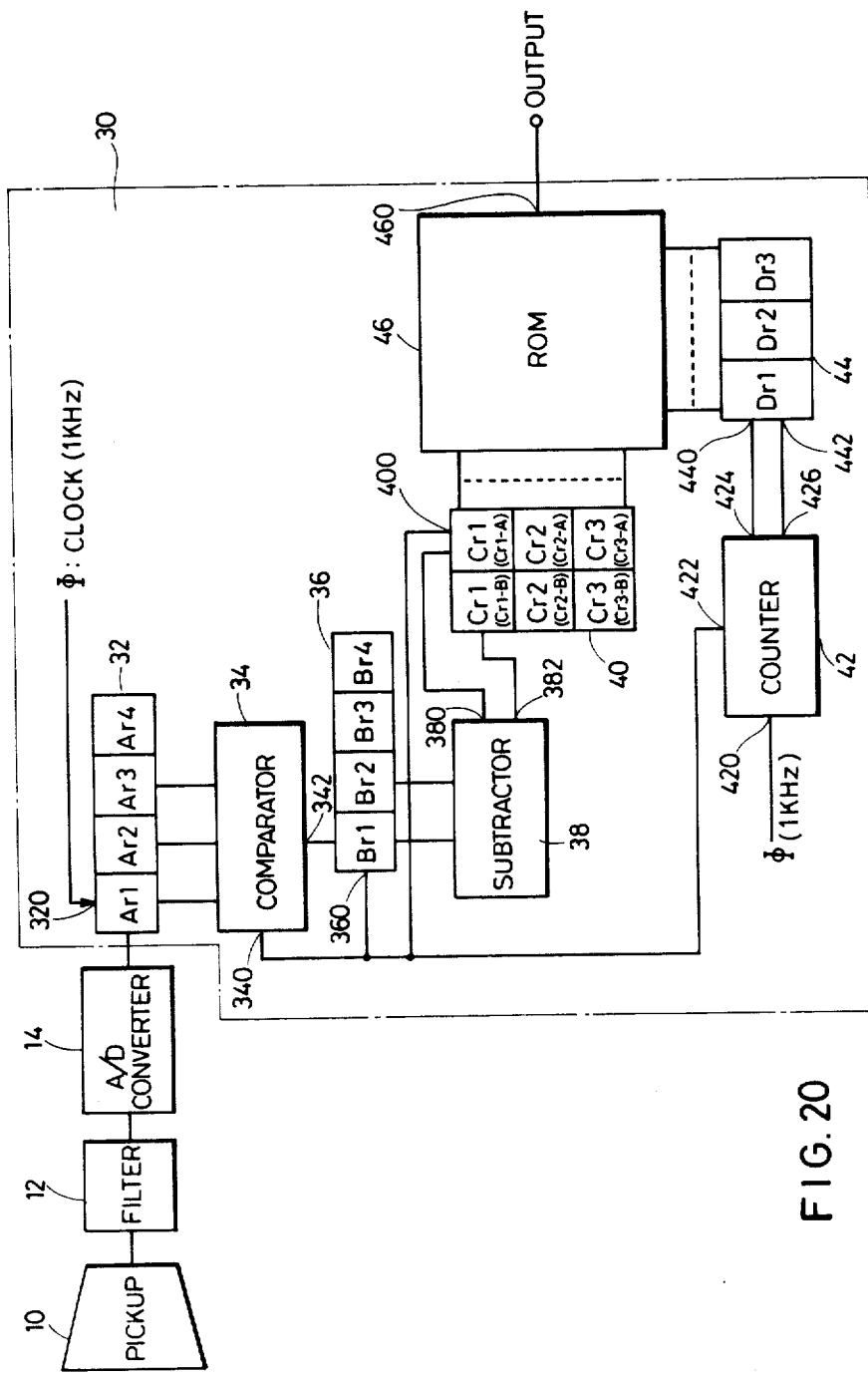
FIG. 20 is a block diagram of another embodiment of an electronic sphygmomanometer according to the present invention.

FIG. 20 shows another embodiment of an electronic sphygmomanometer of the present invention. Like elements corresponding to those of FIG. 1 are indicated by like numerals.

A Korotkoff sounds recognition system 30 includes shift registers 32 (Ar1, Ar2, Ar3 and Ar4) to which the eight bit digital signal is introduced from the analog-to-digital converter 14. Each of the shift registers 32 (Ar1, Ar2, Ar3 and Ar4) is of eight bit construction. A clock pulse ∅ (1 kHz) is applied to a terminal 320 to control the shift operation and the data read operation of the shift registers 32. That is, the digital value developed from the analog-to-digital converter 14 is introduced into the shift registers 32 with the time interval of 1 msec. The three items of eight bit data stored in the shift registers Ar1, Ar2 and Ar3 are introduced into a comparator 34 for checking the characteristics of the filter output signal. When Ar2-Ar1≧0 and Ar3-Ar2<0, or when Ar2-Ar1<0 and Ar3-Ar2>0, a pulse signal is developed from a terminal 340, and the eight bit data stored in the register Ar2 is developed from another output terminal 342.

The eight bit data item developed from the output terminal 342 of the comparator 34 is introduced into shift registers 36 (Br1, Br2, Br3 and Br4) each of which is of eight bit construction. The pulse signal developed from the terminal 340 of the comparator 34 is applied to an input terminal 360 of the shift registers 36 in order to control the shift operation in the shift registers 36 and to introduce the eight bit data developed from the output terminal 342 of the comparator 34 into the shift register Br1. A subtractor 38 is connected to the shift registers Br1 and Br2 to subtract the data stored in the shift register Br2 from the data stored in the shift register Br1. The calculation result (Br1-Br2) is developed from a first output terminal 380, and a second output terminal 382 develops a borrow signal for obtaining a parameter required in the following stage. When (Br1-Br2)≧0, the barrow signal bears the logic "H". When (Br1-Br2)<0, the borrow signal bears the logic "L". The calculation result developed from the subtractor 38 is applied to shift register 40(Cr1, Cr2 and Cr3) for storing purposes. Each of the shift register (Cr1, Cr2 and Cr3) is of nine bit construction. When the pulse signal developed from the terminal 340 of the comparator 34 is applied to an input terminal 400 of the shift registers 40, the shift registers 40 perform the shift operation in order to introduce the calculation result (Br1-Br2) developed from the first output terminal 380 of the subtractor 38 into the shift register Cr1-A. The borrow signal developed from the second output terminal 382 of the subtractor 38 is introduced into the shift register Cr1-B.

A twelve bit counter 42 is provided for calculating the parameter. The above-mentioned clock pulse ∅ (1 KHz) is applied to a first input terminal 420 of the counter 42. When the pulse signal developed from the terminal 340 of the comparator 34 is applied to a second input terminal 422 of the counter 42, the counter 42 develops a control signal at a first output terminal 424 and develops the counted contents at a second output terminal 426. Then, the count contents are reset to zero.

The counted contents developed from the second output terminal 426 of the counter 42 are introduced into shift registers 44 (Dr1, Dr2 and Dr3) each of which are of twelve bit construction. When the control signal developed from the first output terminal 424 of the counter 42 is applied to a first input terminal 440 of the shift registers 44, the shift registers 44 perform the shift operation and memorize the counted contents developed from the second output terminal 426 of the counter 42 in the shift register Dr1 via a second input terminal 442.

The shift registers 40 and 44 function as address circuits for a read only memory 46. The read only memory 46 develops a signal through an output terminal 460 in response to the contents stored in the shift registers 40 and 44. The signal developed from the output terminal 460 of the read only memory 46 takes the logic "H" when the address selected by the shift registers 40 and 44 stores a data "1" which represents that the data relates to the Korotkoff sounds. When the selected address stores the data "0", the signal developed from the output terminal 460 bears the logic "L". The read only memory 46 has the capacity of $2^{(36+48)}$ bits. The read only memory 46 is constructed to store "1" at preselected addresses.

More specifically, since the Korotkoff sounds can be represented by exemplified combinations of the contents stored in the shift registers 40 and 44, the data "1" is set at addresses which correspond to the exemplified combinations.

In a preferred form, the data "1" is set at the addresses corresponding to the following combinations of the contents of the shift registers 40 and 44.

TABLE I

| SHIFT REGISTER | CONTENTS (RANGE) |
|---|---|
| Cr1 | $100_H$–$1BF_H$ |
| Cr2 | $040_H$–$0FF_H$ |
| Cr3 | $100_H$–$1EF_H$ |
| Dr1 | $001_H$–$080_H$ |
| Dr2 | $001_H$–$080_H$ |
| Dr3 | $001_H$–$0C0_H$ |

(represented by Hexadecimal Notation)

That is, the data "1" is stored at the addresses which correspond to the positions where the contents of the shift register Cr1 are between $100_H$ and $1BF_H$, and the contents of the shift register Cr2 are between $040_H$ and $0FF_H$, and the contents of the shift register Cr3 are between $100_H$ and $1FF_H$. These three conditions must be satisfied. Furthermore, the contents stored in the shift registers 44 must satisfy the following three conditions. The contents stored in the shift register Dr1 are between $001_H$ and $080_H$, and the contents stored in the shift register Dr2 are between $001_H$ and $080_H$, and the contents stored in the shift register Dr3 are between $001_H$ and $0C0_H$. Addresses other than the positions which satisfy the above-mentioned six conditions store the data "0".

Figure 21:
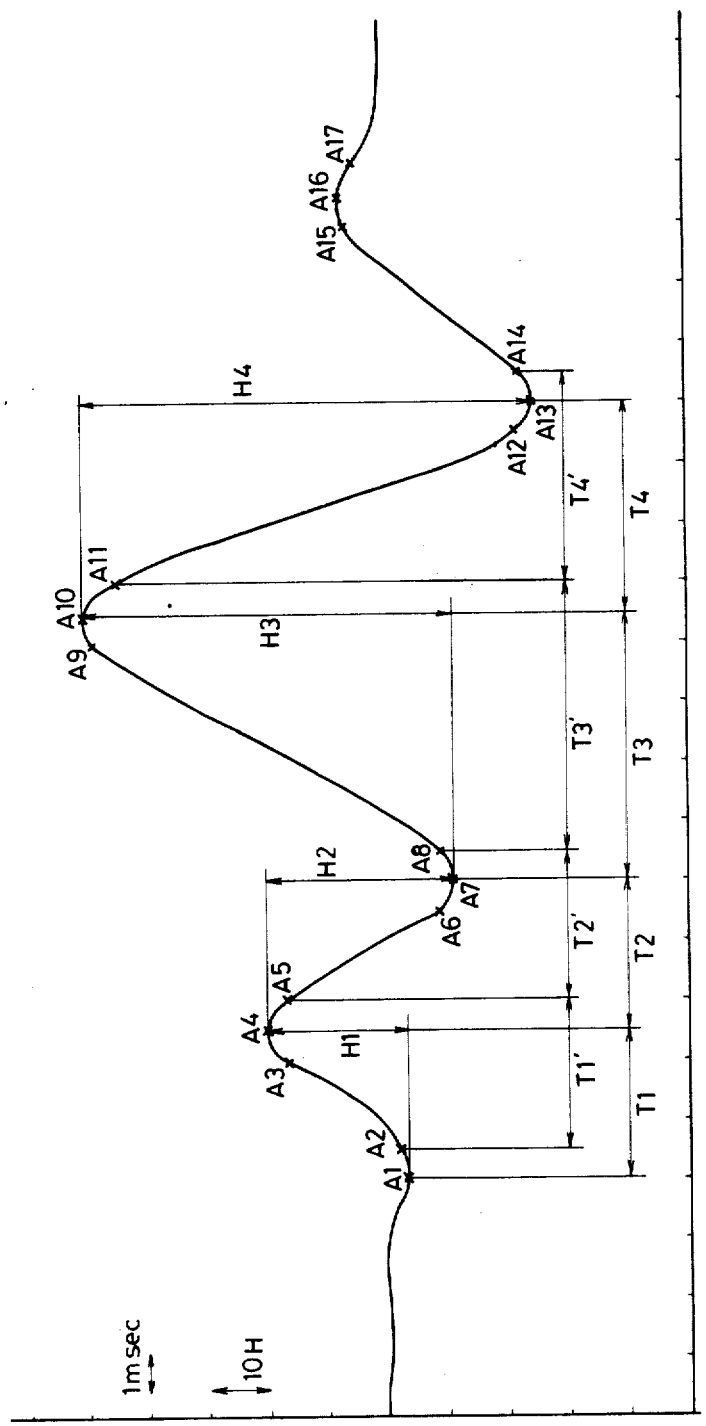
FIG. 21 is an enlarged graph of an output signal of a filter included in the electronic sphygmomanometer of FIG. 20.

An operation of the system shown in FIG. 20 will be described with reference to FIG. 21. In FIG. 21 one abscissa scale indicates 2 msec. and one ordinate scale indicates $10_H$. FIG. 21 shows a filter output signal developed from the filter 12, which is applied to the Korotkoff sounds recognition system 30 via the analog-to-digital converter 14.

When the digital value representing the level of the point $A_5$ is introduced into the shift register Ar1 via the analog-to-digital converter 14, the shift register Ar2 stores the digital value representing the level of the point $A_4$ and the shift register Ar3 stores the digital value representing the level of the point $A_3$. Because $(Ar2-Ar1)\geq 0$ and $(Ar3-Ar2)<0$, the comparator 34 develops the pulse signal from the terminal 340. Accordingly, the shift register Br1 stores the digital value representing the level of the point $A_4$, which has been stored in the shift register Ar2. At this moment, the shift register Br2 stores the digital value representing the level of the point $A_1$. Thus, in response to the output signal from the subtractor 38, the shift register Cr1 stores the digital value representing the difference $H_1$ between the positive (leading edge) peak $A_4$ and the negative (trailing edge) peak $A_1$. Furthermore, the shift register Dr1 stores the time difference $T_1'(=T_1)$ between the two peaks $A_1$ and $A_4$.

Similarly, when the digital value representing the level of the point $A_{14}$ is introduced into the shift register Ar1, the shift registers 40 and 44 store the following values.

shift register Cr1—the difference $H_4$
shift register Cr2—the difference $H_3$
shift register Cr3—the difference $H_2$
shift register Dr1—time difference $T_4'(=T_4)$
shift register Dr2—time difference $T_3'(=T_3)$
shift register Dr3—time difference $T_2'(=T_2)$ When the filter output signal shown in FIG. 2(B) is introduced into the Korotkoff sounds recognition system 30 through the analog-to-digital converter 14, the contents stored in the shift register Cr2 will not be higher than $040_H$ because the filter output signal does not include the peak which has the level higher than 0.8 scale. In FIG. 2(B) one ordinate scale represents the level of $50_H$. Accordingly, the signal developed from the output terminal 460 of the read only memory 46 bears the logic "L".

When the filter output signal shown in FIG. 3(B) is introduced into the Korotkoff sounds recognition system 30 through the analog-to-digital converter 14, at a time when the digital value representing the level of the point d is stored in the shift register Ar2, the shift register Cr1 stores the difference between the peaks d and c, namely about $1AF_H$. The shift register Cr2 stores the difference between the peaks c and b, namely about $040_H$. The shift register Cr3 stores the difference between the peaks b and a, namely about $1EF_H$. Furthermore, the shift register Dr1 stores the time difference between the peaks d and c, namely about $50_{(10)}$. The shift register Dr2 stores the time difference between the peaks c and b, namely about $60_{(10)}$. The shift register Dr3 stores the time difference between the peaks b and a, namely about $40_{(10)}$. These values stored in the shift registers 40 and 44 are included within the range shown in the TABLE I and, therefore, the signal developed from the output terminal 460 of the read only memory 46 bears the logic "H".

Figure 4B:
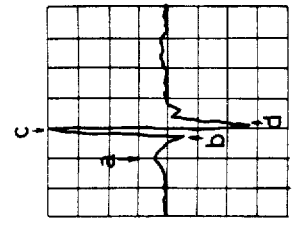

When the filter output signal shown in FIG. 4(B) is introduced into the Korotkoff sounds recognition system 30 through the analog-to-digital converter 14, the shift registers 40 and 44 store the following values at a time when the digital value representing the level of the point d is introduced into the shift register Ar2.

shift register Cr1—about $100_H$
shift register Cr2—about $0A0_H$
shift register Cr3—about $1AF_H$
shift register Dr1—about $30_{(10)}$
shift register Dr2—about $30_{(10)}$
shift register Dr3—about $70_{(10)}$ Since these values are included within the range shown in the TABLE I, the signal developed from the output terminal 460 of the read only memory 46 bears the logic "H".

Figure 5B:
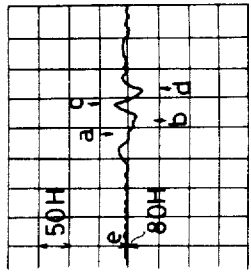

When the filter output signal shown in FIG. 5(B) is introduced into the Korotkoff sounds recognition system 30 through the analog-to-digital converter 14, the shift registers 40 and 44 store the following values at a time when the digital value of the point d is introduced into the shift register Ar2.

shift register Cr1—about $13F_H$
shift register Cr2—about $060_H$
shift register Cr3—about $1E8_H$
shift register Dr1—about $20_{(10)}$
shift register Dr2—about $15_{(10)}$
shift register Dr3—about $20_{(10)}$ Since these values are included within the range shown in the Table I, the Korotkoff sounds recognition system 30 recognizes that the introduced signal relates to the Korotkoff sounds and the signal developed from the output terminal 460 of the read only memory 46 bears the logic "H".

When the filter output signal shown in FIG. 6(B) is introduced into the Korotkoff sounds recognition system 30 through the analog-to-digital converter 14, the shift registers 40 and 44 store the following values at a time when the digital value of the point d is stored in the shift register Ar2.

shift register Cr1—about $18F_H$
shift register Cr2—about $040_H$
shift register Cr3—about $1F8_H$ In this case, the contents stored in the shift register Cr3 are not included within the range $100_H$ through $1EF_H$ shown in the TABLE I. Accordingly, the signal developed from the output terminal 460 of the read only memory 46 bears the logic "L".

In a same manner, when the filter output signals shown in FIGS. 8(B), 9(B), 10(B), 13(B), 14(B) and 15(B) are introduced into the Korotkoff sounds recognition system 30, the signal developed from the output terminal 460 of the read only memory 46 bears the logic "H". When the filter output signals shown in FIGS. 7(B), 11(B), 12(B) and 16(B) are introduced into the Korotkoff sounds recognition system 30, the signal developed from the output terminal 460 of the read only memory 46 bears the logic "L".

In the embodiment of FIG. 1, the determination system 16 is implemented with a one chip microcomputer which includes the central processor unit 18, the read only memory 20, the random access memory 22 and the timer 24.

FIG. 22 schematically shows still another embodiment of an electronic sphygmomanometer of the present invention, wherein an analog-to-digital converter 50 and a digital filter 52 are included in the determination system 16 made of a single chip LSI.

FIG. 23 schematically shows yet another embodiment of an electronic sphygmomanometer of the present invention. Like elements corresponding to those of FIG. 1 are indicated by like numerals. In this embodiment, an amplifier 54 is disposed between the pickup sensor 10 and the filter 12 to amplify the output signal developed from the pickup sensor 10.

FIG. 24 schematically shows a further embodiment of the present invention wherein an analog-to-digital converter 56 is incorporated in the single chip LSI 16. The filter 12 is not included in the determination system 16.

The invention being thus described, it will be obvious that the same may be varied in many ways. Such variations are not to be regarded as a departure from the spirit and scope of the invention, and all such modifications are intended to be included within the scope of the following claims.

What is claimed is:

1. An electronic sphygmomanometer comprising:
   sensor means for detecting sounds or vibrations generated from an artery and for producing an analog output signal;
   analog-to-digital converter means for converting said analog output signal developed from said sensor means into a digital signal; and
   Korotkoff sounds recognition means for analyzing the waveform of said analog signal including:
   monitoring means for introducing said digital signal developed from said analog-to-digital converter means to said Korotkoff sounds recognition means within a preselected time interval;
   detection means for detecting positive and negative peaks in said digital signal introduced by said monitoring means;
   first determination means for determining whether adjacent positive and negative peaks detected by said detection means have a level difference greater than a preselected difference; and
   second determination means for determining whether said adjacent positive and negative peaks are detected by said detection means within a predetermined period of time.

2. The electronic sphygmomanometer of claim 1 further comprising a bandpass filter disposed between said sensor means and said analog-to-digital converter means.

3. A Korotkoff sounds recognition system in an electronic sphygmomanometer comprising:
   analog-to-digital converter means for converting an analog signal developed from sensor means disposed below an arm cuff of the sphygmomanometer digital data representing the level of said analog signal;
   storage means for storing said digital data developed from said analog-to-digital converter means;
   first control means for introducing said digital data developed from said analog-to-digital converter means into said storage means within a preselected time interval;
   first detection means for detecting a first negative (trailing edge) peak in said digital data stored in said storage means;
   second detection means for detecting a positive (leading edge) peak in said digital data stored in said storage means;
   first determination means for determining whether said positive (leading edge) peak detected by said second detection means has a level higher than said first negative (trailing edge) peak detected by said first detection means by an amount greater than a preselected value;
   second determination means for determining whether said positive (leading edge) peak is detected by said second detection means within a preselected period of time after detection of said first negative (trailing edge) peak by said first detection means; and
   second control means for developing a Korotkoff sounds detection signal when said first and second determination means provide affirmative answers.

4. The Korotkoff sounds recognition system of claim 3, wherein said storage means, first and second control means, first and second detection means, and first and second determination means are incorporated in a single chip large scale integrated circuit.

* * * * *